United States Patent [19]

Rada

[11] Patent Number: 4,752,347

[45] Date of Patent: Jun. 21, 1988

[54] APPARATUS FOR PREPARING TISSUE SECTIONS

[76] Inventor: David C. Rada, 6347 Outlook, Mission, Kans. 66202

[21] Appl. No.: 99,306

[22] Filed: Sep. 21, 1987

Related U.S. Application Data

[63] Continuation-in-part of Ser. No. 914,814, Oct. 3, 1986, Pat. No. 4,695,339.

[51] Int. Cl.$^4$ .................. B32B 31/04; B32B 31/20
[52] U.S. Cl. ...................... 156/382; 62/341; 156/390; 156/498; 156/556; 156/884; 269/21; 83/915.5; 425/388; 425/405 R
[58] Field of Search ............... 269/21, 7; 83/915.5, 83/170, 15; 156/80, 57, 379, 341, 344, 285–286, 108, 152, 242, 248, 250, 289, 298, 299, 381–382, 498, 510, 556, 245, 390, 391, 247, 500, 501, 584; 425/388, 405 R, D19, D60; 264/101, 102, 511, 519, 521, D78; 279/3; 62/341, 268, DIG. 7

[56] References Cited

U.S. PATENT DOCUMENTS

| | | |
|---|---|---|
| 3,218,896 | 11/1965 | McCormick . |
| 3,520,055 | 7/1970 | Jannett . |
| 3,598,006 | 8/1971 | Gerber . |
| 3,654,019 | 4/1972 | Cusik . |
| 3,667,330 | 6/1972 | Kobernick . |
| 3,737,335 | 6/1973 | Feinberg . |
| 3,742,802 | 7/1973 | Moevz . |
| 3,765,289 | 10/1973 | Gerber . |
| 3,803,958 | 4/1974 | Fernandez-Moran . |
| 3,832,923 | 9/1974 | Lossmann et al. . |
| 4,012,475 | 3/1977 | Kindel . |
| 4,060,440 | 11/1977 | Behme . |
| 4,190,472 | 2/1980 | Slonicki . |
| 4,532,838 | 8/1985 | Soderkvist . |
| 4,543,867 | 10/1985 | Levene . |
| 4,545,831 | 10/1985 | Ornstein . |

OTHER PUBLICATIONS

Evaluation of a Method for Controlled Tissue Embedding for Histologic Evaluation of Tumor Margins, Gormley, Daniel E., Md, American Journal of Dermato pathology,9(4): 308–315, 1987.
Hanke et al., "Chemosurgical Reports: Frozen-Section Processing with the Miami Special"; J. Dermatol. Surg. Oncol, vol. 9, No. 4, Apr. 1983, pp. 260–262.
Swanson "Mohs Surgery"; Arch. Dermatol., vol. 119, Sep. 1983, pp. 761–772.
Carter "A New Method for Preparing Tissue Blocks for Cryostat Sectioning"; J. Dermatol. Surg. Oncol., vol. 11, No. 7, Jul. 1985, pp. 687–689.
Conception "How to Prepare Tissue Blocks (published as letter to the Editor) J. Dermatol. Surg. Oncol., vol. 12, No. 2, Feb. 1986, pp. 112,113.
Picoto "Technical Procedures for Mohs Fresh Tissue Surgery", J. Dermatol. Surg. Oncol., vol. 12, No. 2, Feb. 1986, pp. 134–138.

Primary Examiner—Merrell C. Cashion, Jr.
Attorney, Agent, or Firm—Litman, McMahon & Brown

[57] ABSTRACT

A method and apparatus for preparing a tissue block for sectioning in a microtome includes positioning the tissue block on a platform. A vacuum-retracted membrane of plastic film material is used to draw an underside of the tissue block or specimen into planar contact with the platform. The user adjusts any peripheral edges of the tissue block that are not properly oriented so the underside is in a planar position. The tissue block is frozen on the platform once it is properly oriented. The membrane is subsequently peeled away from the platform and O.C.T. compound is applied to the tissue blocks. The O.C.T. compound after hardening and the tissue block are transferred to a second platform carried by a mounting device such that the tissue underside is exposed. The tissue specimen is ready for sectioning as part of the Mohs fresh tissue surgical technique.

16 Claims, 6 Drawing Sheets

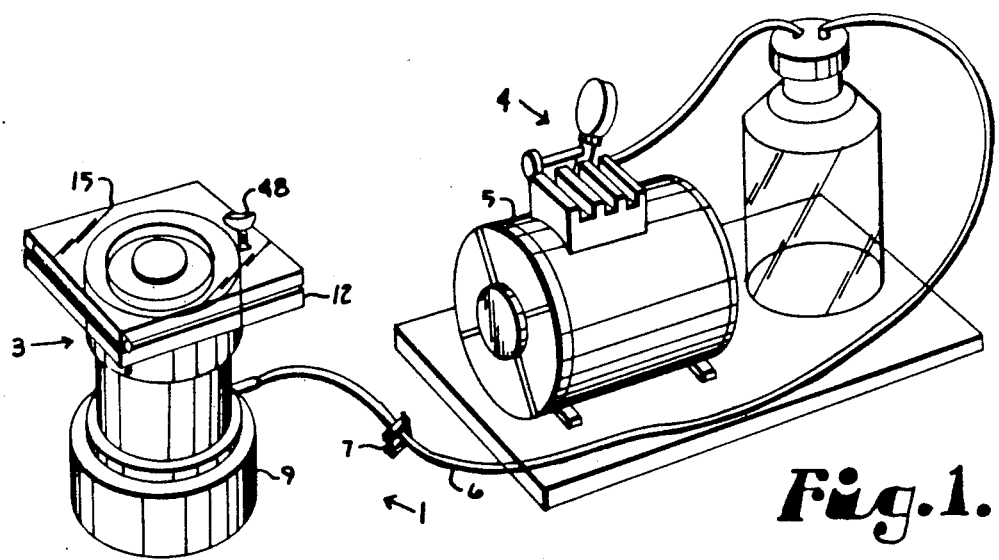
Fig.1.
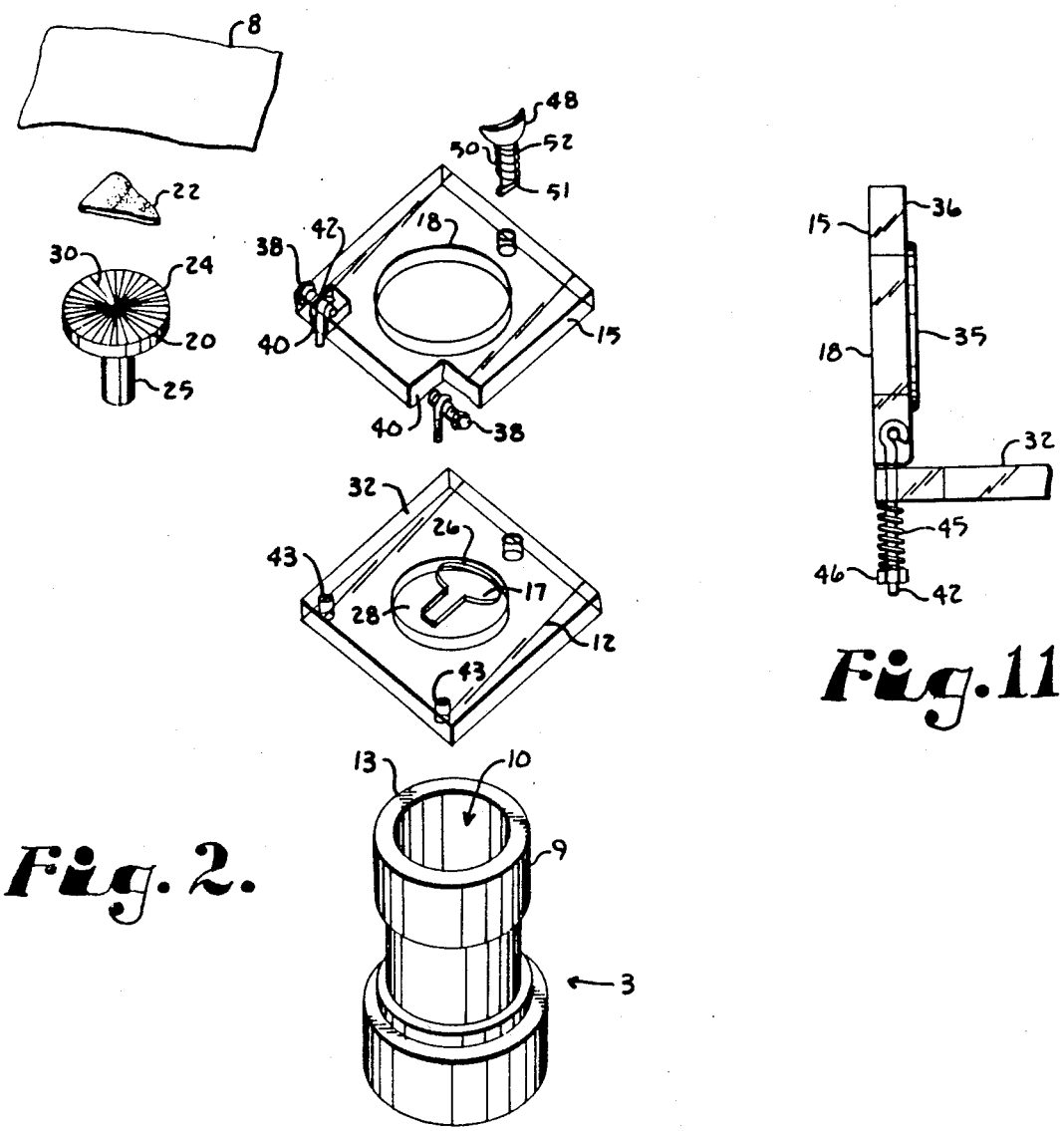
Fig.11.
Fig.2.

Fig.6.
Fig.7.
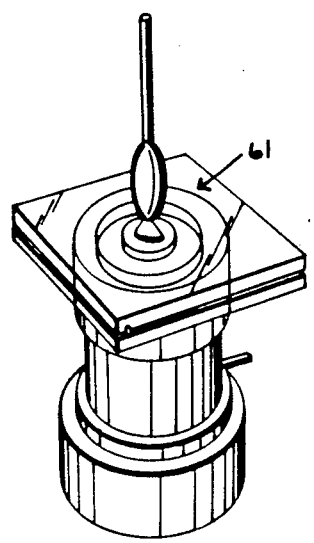
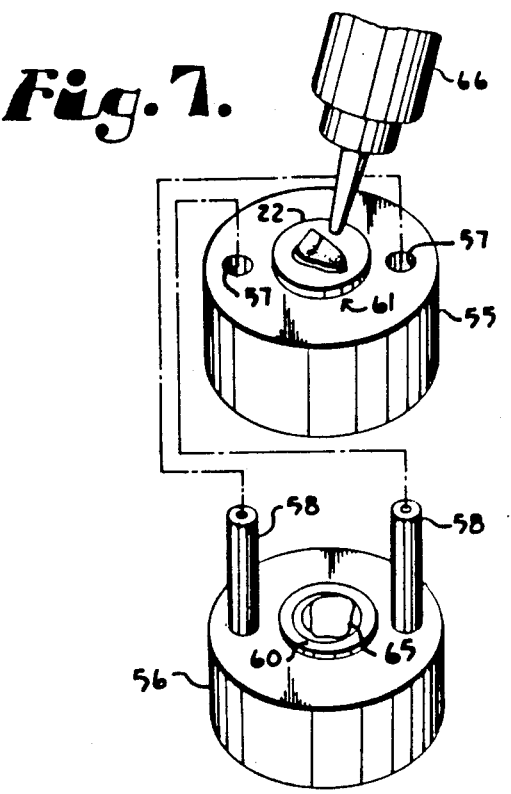
Fig.8.
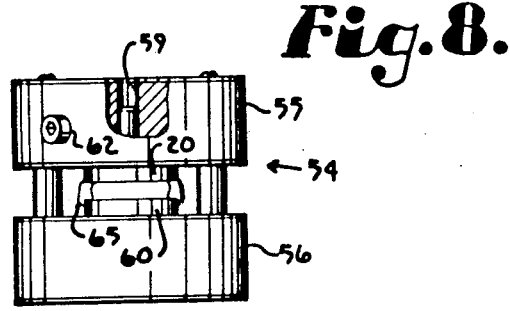
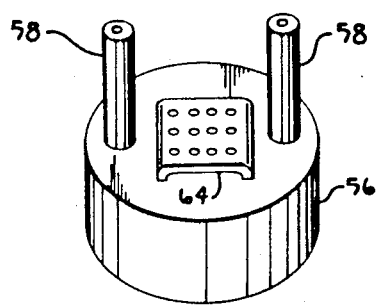
Fig.10.
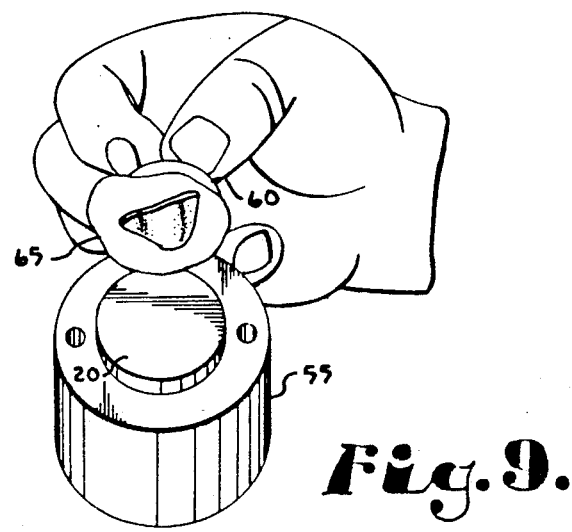
Fig.9.

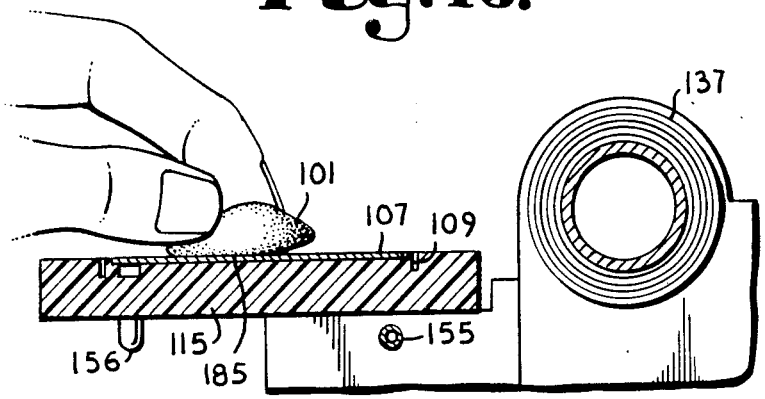
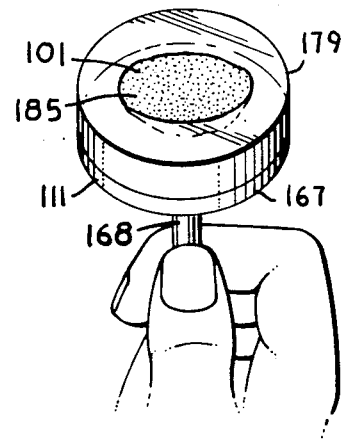
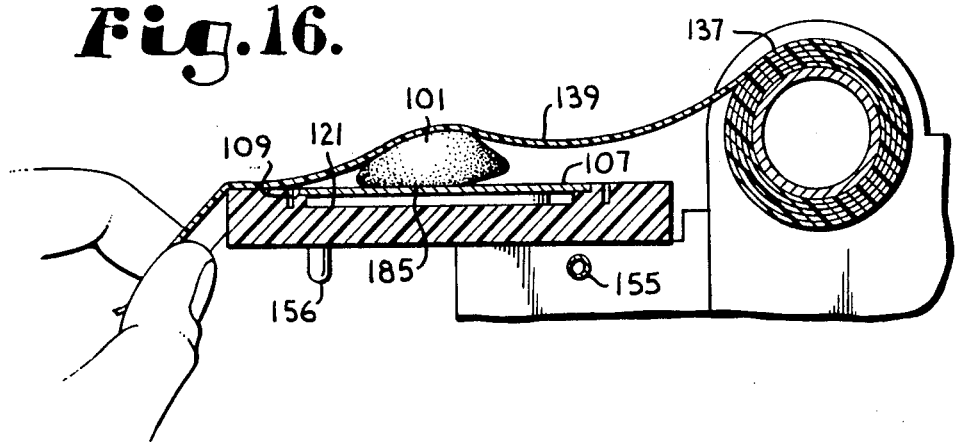
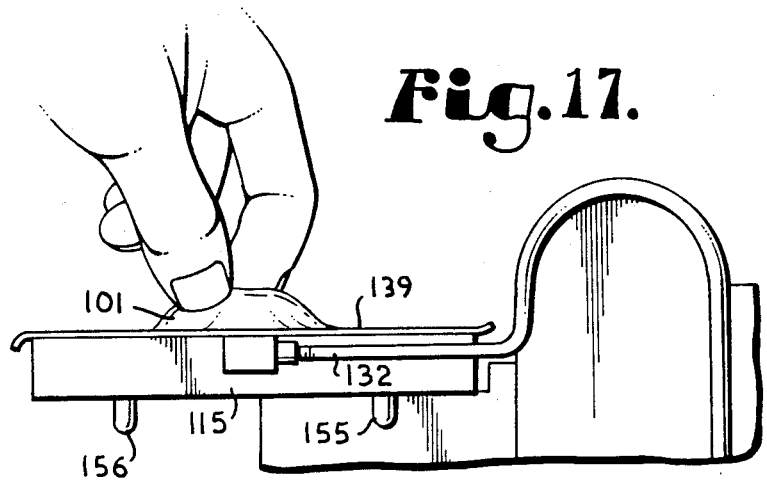
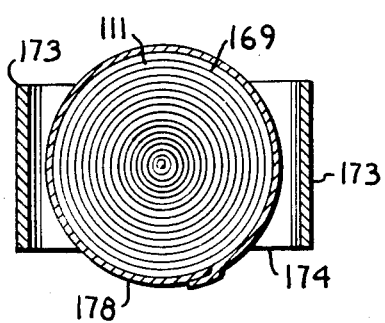

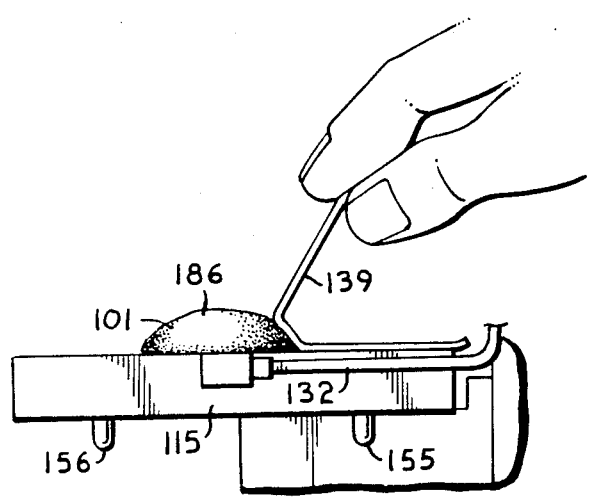
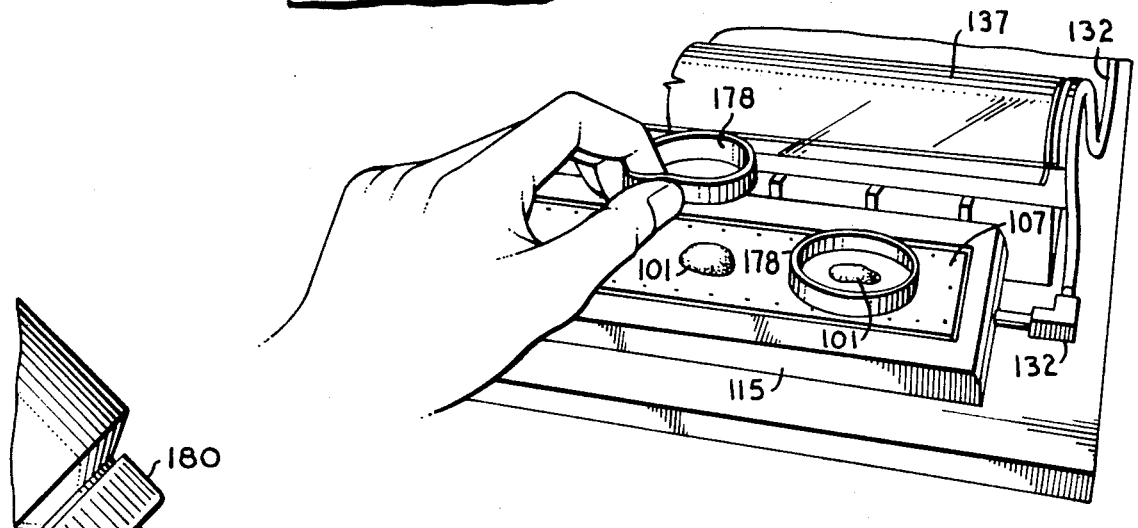
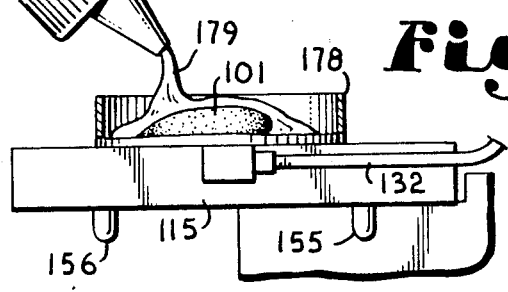
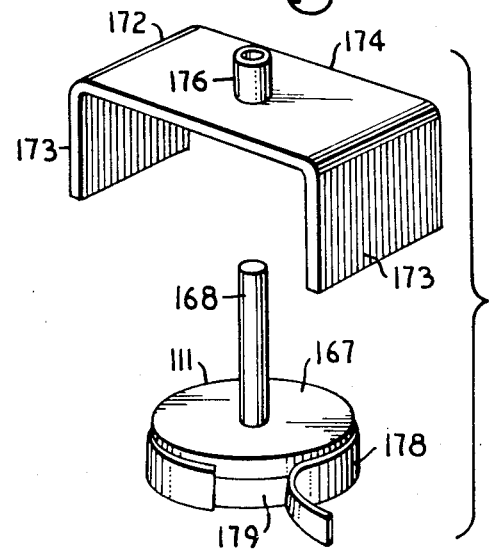
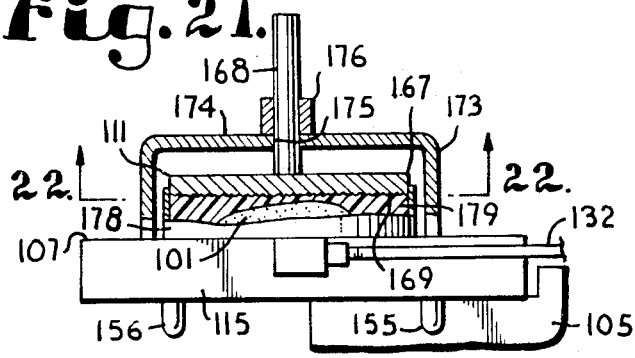

APPARATUS FOR PREPARING TISSUE SECTIONS

CROSS-REFERENCE TO RELATED APPLICATION

The present application is a continuation-in-part of U.S. Ser. No. 914,814 filed Oct. 3, 1986 entitled METHOD FOR PREPARING TISSUE SECTIONS, now U.S. Pat. No. 4,695,339 issued Sept. 22, 1987.

BACKGROUND OF THE INVENTION

This invention relates to the preparation of tissue blocks for sectioning and specifically to preparation for tissue sectioning incidental to the Mohs fresh tissue surgical technique.

In Mohs fresh tissue surgery, cutaneous malignancies and certain major carcinomas of the head and neck are excised using microscopic control. The key to Mohs surgery is the production of high quality, horizontally cut frozen tissue sections, which are subsequently microscopically reviewed to determine whether any residual tumor is present. Initially, the cancerous area is debulked and an amount of tissue is excised. The surgical area has been scored with a scalpel or otherwise mapped for orientation purposes. The scoring will properly orient the surgeon as he or she performs additional excisions as indicated by the results of an inspection of a microscopic section of the excised tissue. Any residual tumor that is indicated by the microscopic inspection is then excised, and the procedure is repeated until all sections are negative. The excised tissue block is generally of curved, or parabolic, cross-section and must be converted to a planar cross-section for the cryostatic sectioning. Past techniques have attempted in various ways to obtain a planar section, including freezing of the tissue to a flat polished disc after attempting to roll it flat by use of a scalpel or specially prepared forceps. In the utilization of previous techniques, a technician had to adjust specimen edges that were reluctant to flatten. The manual procedures used were cumbersome and difficult to effect. Typically, they required excellent hand and eye coordination, since the specimen was not easily manipulatable.

The tissue block is subsequently inked and sections are cut to a thickness between five and seven micrometers. After staining, each section is microscopically examined by the surgeon, who interprets the results on-site, thus saving critical time. Residual neoplasm, when observed in the first microscopic section, indicates further excision is necessary. This process is repeated until no further tumor is found upon microscopic examination. The Mohs surgery permits the maximum preservation of normal surrounding tissue, and the defect remaining after total cancer removal can be immediately reconstructed.

In order to obtain tissue sections that are satisfactory for microscopic examination through the use of the microtome (also known as a cryostat) the face of the specimen to be sectioned should be planar and parallel to the path of relative movement between the microtome knife and the specimen, thus ensuring sections of uniform thickness suitable for microscopic examination.

Preorientation of the mounted tissue so that the planar surface is parallel to the knife path reduces the cutting time involved in that the microtome chuck does not need to be adjusted. The surface presented by the frozen specimen is generally of irregular contour and, using prior techniques, some trimming of the specimen is necessary in order to provide the face of the specimen with a suitable surface. This has been found to be true even when special techniques have been utilized to flatten the peripheral portions of the tissue into plane with the central portion thereof. It is frequently difficult to freeze the specimen to the cryostat disc in an orientation that best presents the tissue block for cutting along the most desirable section. Prior positioning and manipulative techniques have been found to be lacking in terms of ease and reliability of manipulation.

OBJECTS OF THE INVENTION

The principal objects of the present invention are: to provide an improved method and apparatus for preparing tissue sections; to provide such a method and apparatus for presenting a tissue block for sectioning by a microtome; to provide such a method and apparatus which precisely orient frozen tissue blocks for sectioning; to provide such a method and apparatus which use a vacuum-retracted membrane to orient the undersurface and peripheral margin of the tissue block for optimum positioning; to provide such a method and apparatus which facilitate manipulation of the tissue block for optimum positioning; to provide such a method and apparatus which are time and cost effective, so as to reduce the overall surgical time and expense necessary to effect the total excision of the malignancy; to provide such a method and apparatus which are relatively simple to use, economical to manufacture, and particularly well adapted for the proposed usage thereof.

Other objects and advantages of this invention will become apparent from the following description taken in conjunction with the accompanying drawings wherein are set forth, by way of illustration and example, certain embodiments of this invention.

SUMMARY OF THE INVENTION

A system for preparing tissue blocks for presentation to a microtome for sectioning is provided. A tissue block, or specimen, is inked or marked by conventional methods to provide later "landmarks" compared to the excision site and placed on a polished platform, with a tissue surface to be examined against the polished surface. The system is designed to facilitate the rapid production of uniform frozen sections used in Mohs microcontrolled fresh tissue surgery.

The platform, with specimen thereon, is placed into a vacuum receptacle assembly and covered by a flexible plastic membrane. Alternatively, the platform has surface slots communicating with a vacuum generating device to produce a vacuum therein and draw the membrane tightly against the specimen and exposed portion of an upper surface of the platform. The receptacle assembly may be provided with multiple receptacles for receiving multiple platform/specimen complexes for simultaneous processing. The plastic membrane is preferably a polyethylene plastic sheet material and may be fed through a dispenser slot to the operator. A hood, or cover plate, with access means may be provided to form a seal between the membrane and the vacuum receptacle body. A vacuum source of the vacuum receptacle assembly is activated and evacuates air from between the membrane and the tissue block, flattening the block into a planar unit. At this point, the operator can manipulate the specimen to achieve the most advantageous position on the platform, as determined on a case-bycase basis. Once the tissue block specimen is properly oriented into a flat profile, liquid nitrogen is used to freeze the tissue block to the platform. The liquid nitrogen is swabbed, as with a proctoscopic-type swab, or dripped onto the tissue block for freezing. Alternative refrigerating or freezing means or medium for freezing may be used, including cryogenic freon, nitrous oxide, carbon dioxide or the like and such freezing means may be circulated through a serpentine channel in the platform to chill the platform and consequently the tissue block.

The membrane is peeled away from the platform and the specimen, and in one embodiment an embedding medium such as O.C.T. compound is applied to the specimen platform and to a mateable corrugated platform. After the O.C.T. compound has partially solidified, the platforms are mated and allowed to solidify. The platforms are subsequently separated, with the tissue block being retained by the corrugated platform, through interaction of the O.C.T. compound and the rough surface of the corrugated platform. Preferably, the specimen platform is provided with an anti-stick formula (such as tetrafluoroethylene, sold by DuPont de Nemours under the trademark Teflon) for ease of removal at this stage. Alternatively, embedding mechanism is placed around the tissue block and a second platform is placed thereon being positioned by a jig to ensure the lower surface of the tissue block is parallel to the surface of the second platform. After the embedding medium hardens, the tissue block is freed from the original platform. The tissue block is then ready for sectioning and presents a solidly frozen, planar surface for ease of microtome sectioning.

The drawings constitute a part of this specification and include exemplary embodiments of the present invention and illustrate various objects and features thereof.

BRIEF DESCRIPTION OF THE DRAWINGS

FIG. 1 is a perspective view of an apparatus for preparing tissue sections according to the present invention.

FIG. 2 is an enlarged, exploded view of a vacuum receptacle, polished platform, tissue block specimen, and plastic membrane according to the present invention.

FIG. 6 is a schematic view showing a later step according to the present invention wherein the tissue block specimen is being frozen.

FIG. 7 is an exploded schematic view of a later step according to the present invention for transferring the tissue block specimen from the polished platform to a corrugated platform.

FIG. 8 is a schematic view of two mounting devices for mating the polished and corrugated platforms for transferring the tissue block specimen from the polished platform to the corrugated platform.

FIG. 9 represents a final step according to the present invention wherein the tissue block specimen has been transferred to the corrugated platform and is embedded in a cutting compound.

FIG. 10 is a perspective view of an alternative type mounting platform.

FIG. 11 is an enlarged, fragmentary side elevational view of the vacuum receptacle showing a hinged cover plate thereof in a raised position.

FIG. 15 is an enlarged and fragmentary side elevational view of the modified apparatus illustrating a step in the method of using the apparatus wherein a tissue sample is placed on the apparatus.

FIG. 16 is an enlarged and fragmentary side elevational view of the modified apparatus and tissue sample, showing a step in the method of using the apparatus wherein a membrane is placed over the tissue sample.

FIG. 17 is an enlarged and fragmentary side elevational view of the modified apparatus and sample, showing a step in the method of using the apparatus wherein the tissue sample is manipulated by an operator.

FIG. 18 is an enlarged and side elevational view of the modified apparatus and tissue sample, showing a step in the method of using the apparatus wherein the membrane is peeled from the tissue sample.

FIG. 19 is a fragmentary perspective view of the modified apparatus and tissue sample, illustrating a step in the method of using the apparatus wherein a collar is placed around a tissue sample and showing another tissue sample with a collar already in place around the sample.

FIG. 20 is an enlarged and fragmentary side elevational view of the modified apparatus, tissue sample and collar, illustrating a step in the method of using the apparatus wherein embedding medium is placed within the collar to surround the tissue sample.

FIG. 21 is an enlarged and fragmentary side elevational view of the modified apparatus, tissue sample, collar and medium, illustrating a step in the method of utilizing the apparatus wherein a platform having a surface is placed over the tissue sample and in touching relationship with the medium, the platform is aligned by a support jig.

FIG. 22 is an enlarged and cross-sectional view of the modified apparatus showing the platform surface and support jig thereof, taken along line 22—22 of FIG. 21.

FIG. 23 is an enlarged perspective view of the modified apparatus showing the platform, support jig, tissue sample and collar, and illustrating a step in the method of use of the apparatus wherein the collar is peeled from the medium and sample.

FIG. 24 is an enlarged and perspective view of the modified apparatus showing the support platform, medium and tissue sample, and illustrating the tissue sample in a state prepared for further processing, including slicing and examination.

DETAILED DESCRIPTION OF THE INVENTION

Figure 3:
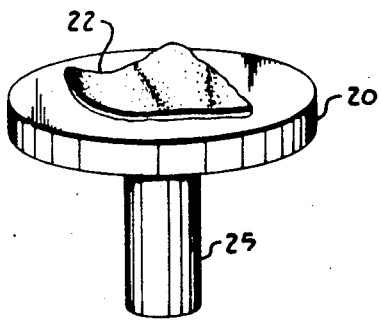
FIG. 3 is an enlarged perspective view of the polished platform showing the tissue block specimen in an original position thereon.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Referring to the drawings in more detail, the reference numeral 1 in FIGS. 1 through 11 generally indicates a retracting and aligning dermal apparatus for preparing tissue sections according to the present invention.

The apparatus 1 includes a vacuum receptacle assembly 3 and a vacuum source 4 as is well-known in the art. The vacuum receptacle assembly 3 is connected to the vacuum source 4, which includes an appropriate vacuum pump 5. A hose 6 operably connects the vacuum source 4 to the vacuum receptacle assembly 3. A clamp 7 is provided to pinch the hose 6 to selectively permit or prevent airflow therethrough. A transparent, flexible membrane 8 is provided for sealing the vacuum receptacle assembly 3 during operation. The receptacle assembly 3 includes a generally cylindrical receptacle structure 9 having an interior chamber 10. The receptacle assembly 3 further includes a baseplate 12 attached to a top portion 13 of the receptacle 9, and a cover plate 15 connected to the baseplate 12 by hinge means. The baseplate 12 and cover plate 15 have respective orifices 17, 18 corresponding in position to the receptacle interior chamber 10 for providing access thereto. Preferably, the baseplate 12 and the cover plate 15 are made of a clear acrylic resin plastic, such as is marketed by DuPont de Nemours under the trademark Lucite, and are illustrated as such.

A polished disc 20 is provided for receiving a tissue block or specimen 22. As used herein, "polished disc" contemplates a disc having a relatively smooth surface. The polished disc 20 includes a planar, circular polished platform 24 and a central stem 25 depending therefrom. The receptacle assembly includes means for receiving the disc. As illustrated, the baseplate orifice 17 is sized to receive the stem 25 therethrough. The baseplate orifice 17 further includes an elliptical section 26, such that the orifice 17 has a generally "key-hole" shape. This shape facilitates the removal of the disc 20 from the orifice 17, by tipping one edge of the platform 24 into the elliptical section 26 of the orifice 17 and grasping a opposed side of the platform 24. The baseplate 12 includes a recessed step portion 28 surrounding the orifice 17 and sized and recessed sufficiently to receive the polished platform 24 in relatively close fitting relation. A surface 30 of the platform 24 is generally flush with an upper surface 32 of the baseplate 12 when the disc 20 is in position.

The hinge means swingably connects the cover plate 15 to the baseplate 12, as illustrated in FIG. 11. The hinge means is spring-loaded to perfect a seal between the membrane 8 and the baseplate 12, in the method described below. In order to achieve this result, a good seal must be maintained between the baseplate 12 and the membrane 8 and simultaneously between the membrane 8 and the cover plate 15. An O-ring 35, is arranged in a surrounding position around the cover plate orifice 18. The O-ring 35 is fixed to an under surface 36 of the cover plate 15, but it could be fixed to the baseplate 12. Taken together, the baseplate 12, cover plate 15, and O-ring 35 constitute sealing means for creating a seal between the membrane 8 and the receptacle assembly 3.

The hinge means include a pair of pivot bolts 38, which extend into the body of the cover plate 15 from opposed sides thereof, as seen in FIG. 2. The pivot bolts 13 extend into slots 40, which are cut into the cover plate 15. The pivot bolts 38 provide means about which spring-loaded bolts 42 swing. The bolts 42 are pivotable about an axis of the pivot bolts 38, extend through respective holes 43 in the baseplate 12 and depend from the baseplate 12. Respective springs 45 are received onto the spring-loaded bolts 42 and held in place by respective nuts 46. The springs 45 tend to bias the cover plate 15 toward the baseplate 12. When the cover plate 15 is in a raised position, as seen in FIG. 11, the spring-loaded bolts 42 will maintain the cover plate 15 in the raised position, allowing the user to position the disc 20.

In a closed, or covering position, the cover plate 15 is generally parallel to the baseplate 12, and the spring-loaded bolts 42 will place an uneven amount of torque on the cover plate 15. To counteract this effect and to further enhance the sealing operation between the base and cover plates 12 and 15, a spring-loaded locking key 48 is provided in a position opposite the bolts 42. The key 48 includes a locking shaft 50 having an oblong locking section 51 thereon. A tension spring 52 is carried on the shaft 50 above the locking section 51, as seen in FIG. 2. The baseplate 12 has an oblong hole therethrough, through which the key 48 can extend. Once the key 48 is inserted through the holes, an approximate 90 degree twist of the key 48 will lock it in place in a spring-loaded manner.

A platform mounting device 54 is used in the present method and includes first and second mounting members 55 and 56, which mate one to the other. The first mounting member has alignment bores 57, which matingly receive corresponding alignment spindles 58 of the second mounting member 56. A central bore 59 extends through the first mounting member 55, as seen in FIG. 8. The polished disc stem 25 is receivable into the bore 59, as will be discussed in more detail below. A set screw 62 is provided for locking the stem 25 in the bore 59, and thus the polished disc 20, in position. The second mounting member 56 also includes a central bore (not shown.)

A corrugated disc 60 includes a stem that is receivable into the second mounting member bore for alignment with the polished disc 20.

An alternative corrugated platform 64 ma be used instead of the corrugated disc 60, depending on the type of microtome or cryostat being utilized in the examination process.

The basic apparatus 1 having been described, the method according to the present invention will now be discussed in detail, with further structural details also being added. The present method utilizes a vacuum-retracted membrane to orient the undersurface and peripheral margin of various tissue specimens, including mucosa, dermis, and cartilage.

FIG. 3 represents an initial step in the present method, wherein the tissue specimen 22 to be examined using horizontal frozen sections per the Mohs technique has been placed onto the polished disc 20. Deep margins of the tissue specimen 22 are inked in the standard Mohs fashion. The inked specimen 22 is placed onto the polished platform 24 such that the surface to be examined for margins is directly against the polished surface. As illustrated, the surface 30 of the platform 24 has been lightly scored radially and has an anti-stick coating thereon such as tetrafluoroethylene-type material. The score lines assist in retracting the plastic membrane, as the score lines allow flow of air across the surface 30. The use of the anti-stick coating obviates the need to apply an anti-stick lubricant, which may be unevenly applied, subsequently resulting in improper release of the specimen 22. However, in some instances where an anti-stick coating is not appropriate, an anti-stick lubricant (such as a spray mixture of soybean oil, alcohol, lecithin and propellant marketed under the trademark PAM) may be used. The disc 20, with tissue specimen 22 thereon, is then placed into the receptacle structure 9. Specifically, the stem 25 is inserted through the orifice 17, generally in the center of the baseplate step portion 28. The platform 24 is received into the step portion 28, which is sized to receive the platform 24 in close relationship. However there is sufficient clearance for air movement into the receptacle chamber 10.

Figure 4:
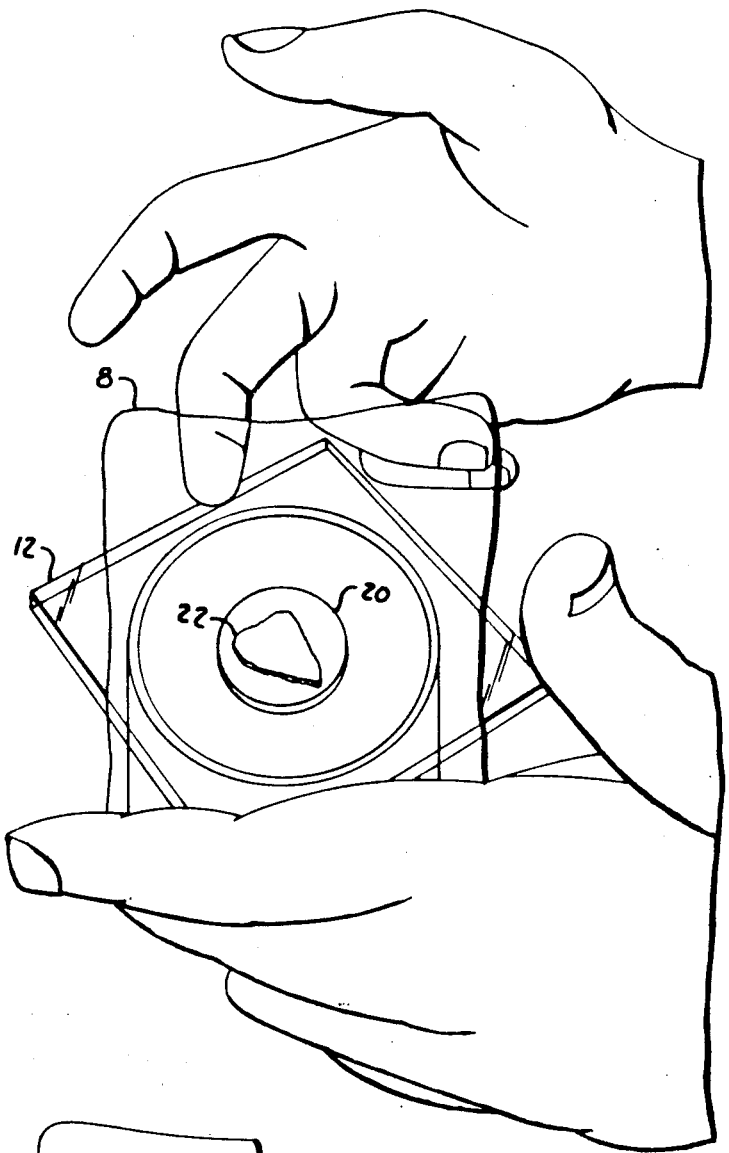
FIG. 4 is a schematic representation of one of the preliminary steps according to the present invention.

FIG. 4 shows the polished disc 20 in place on the baseplate 12, with the tissue block 22 carried on the platform 24. FIG. 4 further represents the membrane 8 being placed over the platform 24 and tissue specimen 22, covering same and extending outwardly therefrom. It is important to ensure that the borders of the membrane 8 extend beyond the seal area of the baseplate 12 covered by the O-ring 35 when the cover plate 15 is brought into contact with the baseplate 12. If the membrane 8 does not extend beyond the O-ring seal area, a faulty seal will result and a new membrane 8 will be necessary.

Figure 5:
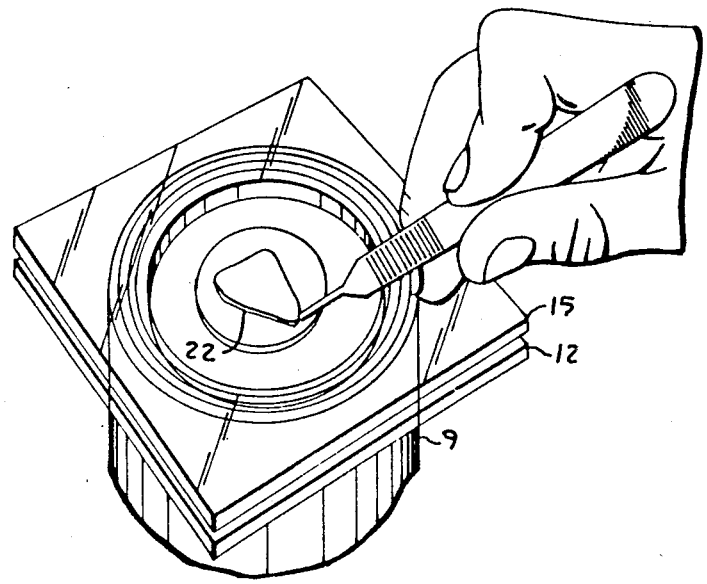
FIG. 5 is a schematic view of a later step according to the present invention and showing manipulation of the tissue block specimen with the plastic membrane in place.
Figure 12:
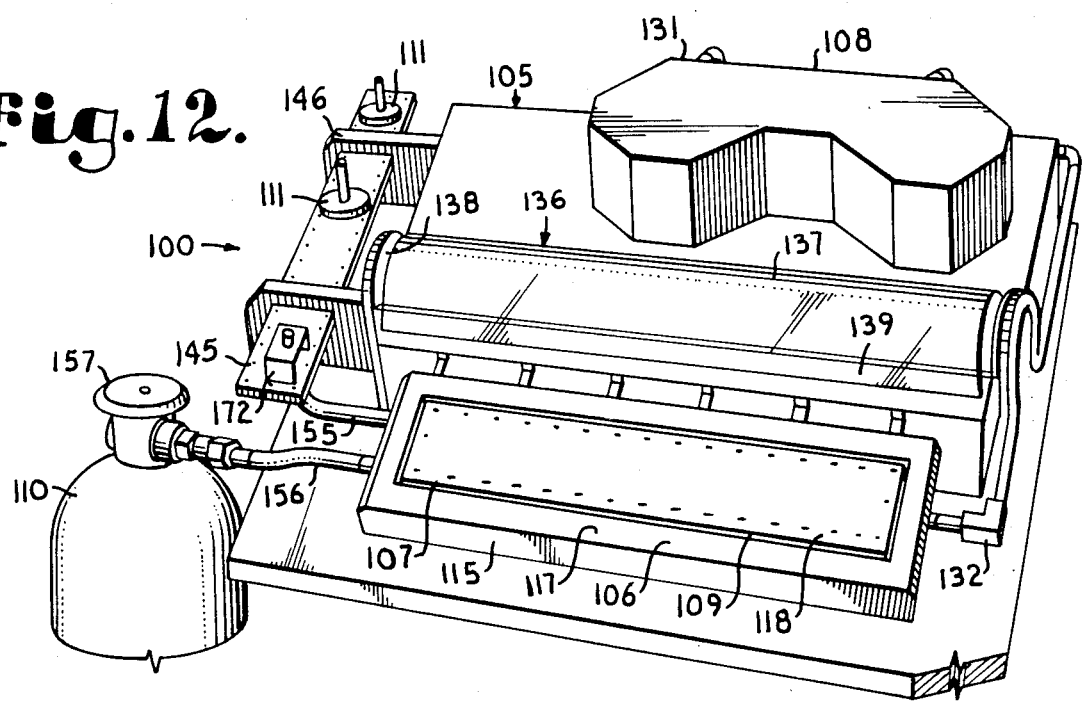
FIG. 12 is a perspective view of a modified apparatus for preparing tissue sections according to the present invention.
Figure 13:
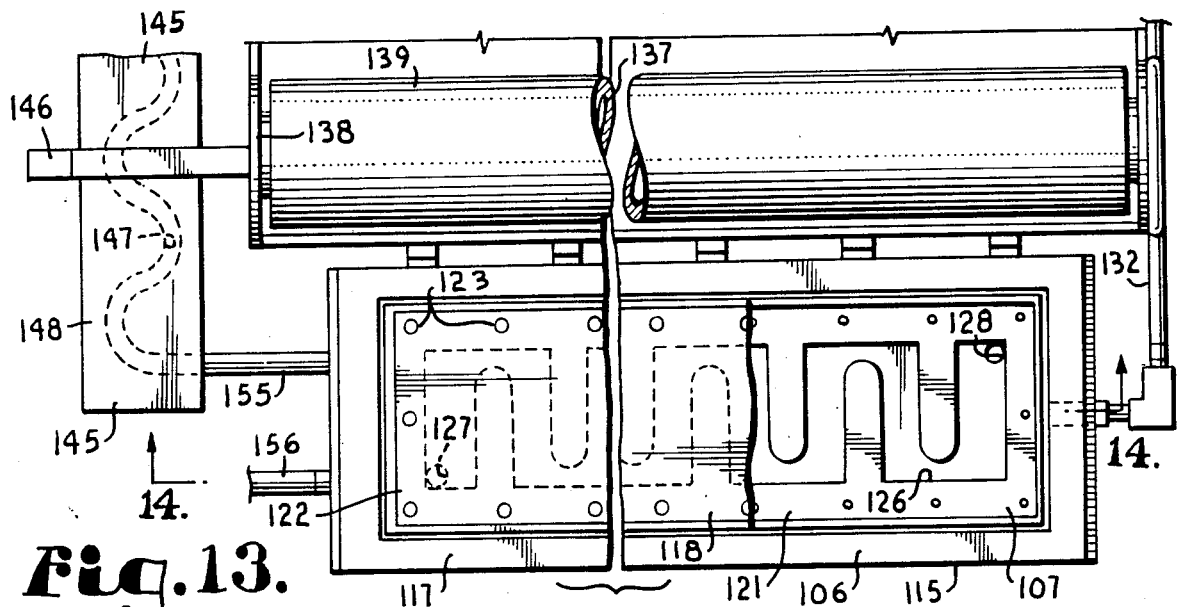
FIG. 13 is an enlarged and fragmentary top plan view of the modified apparatus with portions broken away to show detail thereof.
Figure 14:
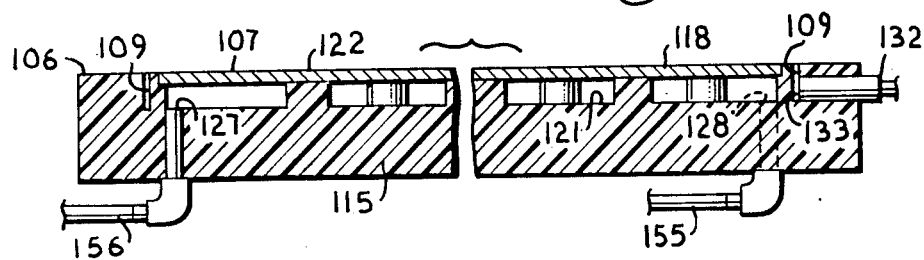
FIG. 14 is an enlarged and fragmentary cross-sectional view of the modified apparatus, taken generally along line 14—14 of FIG. 13.

With the membrane 8 in place, the cover plate 15 is brought into its covering position over the baseplate 12, as seen in FIG. 5. The key 48 is pushed through the corresponding hole in the baseplate 12 and rotated into a locking position. The tissue specimen 22 is inspected to ensure that the desired orientation has not been disturbed during placement of the membrane 8 and securing of the cover plate 15.

The operator then ensures that the clamp 7 is closed and activates the vacuum pump 5. It is envisioned that an alternative foot switching valve or the like may be provided in place of the clamp 7 to regulate the vacuum source 4. The clamp 7 is slowly opened, which allows the vacuum source 4 to draw air from the vacuum receptacle assembly 3, retracting the membrane 8 onto the platform 24. This retraction pulls the edges of the tissue specimen 22 down into a planar orientation parallel to the platform 24. The tissue specimen 22 can then be manipulated by the operator (generally the surgeon), as seen in FIG. 5. Either a medical instrument, as seen in FIG. 5, or the operator's fingers may be used to manipulate the specimen through the membrane until a desired orientation of the tissue specimen 22 is obtained. This manipulation is done while gradually reaching full vacuum of approximately 25 inches of mercury. Upon complete evacuation of the receptacle chamber 10, and the manipulation through the membrane 8, the peripheral edges of the tissue specimen are oriented properly for subsequent tissue sectioning.

The operator should observe ink flow patterns and occlude any running ink streams with the medical instrument or finger. If the peripheral border does not flatten completely, the specimen 22 can be gently secured with the operator's fingers as the edges are gently pressed down to create additional vacuum streams, which will further flatten the edge down.

In the event that the tissue specimen 22 cannot be properly oriented, a new membrane 8 is used and the securing and evacuating steps are repeated. If this is necessary, the membrane should be lifted from side to side at an approximate 30 degree angle to the platform, and a cotton swab used to hold the specimen 22 in place by a transmembrane approach. It is noted that the use of sharp instruments or long fingernails must be avoided during the membrane/specimen manipulation to ensure against leaks. If a leak does occur, the membrane 8 is replaced with a substitute membrane 8. It is also necessary to avoid allowing the specimens to become inflexible due to drying.

In the event that a vacuum receptacle assembly that can accommodate more than one disc 20 is used, it has been found that all of the discs 20 should be in place during the vacuum evacuation, even if not all have tissue specimens thereon.

In FIG. 6, the vacuum alignment and orientation step has been completed and solidification of the tissue specimen 22 is now accomplished. As illustrated, a large swab with liquid nitrogen thereon is used to freeze the tissue specimen 22 to the platform 24. It has been found that proctoscopic-type swabs work well. Freon and other types of freezing agents may also be used, but the freeze is generally less satisfactory than that obtained using the liquid nitrogen.

A frozen polished disc/specimen complex 61 is now removed from the vacuum receptacle assembly 3. The cover plate is released by disengaging the locking key 48 and raised into the upright position. The membrane 8 is grasped and peeled from the specimen 22 at an angle of approximately five to ten degrees from horizontal. If this angle is increased, it has been found that the tissue specimen 22 may separate from the platform 24. After the membrane 8 is removed, the disc/specimen complex 61 is removed by tipping one side of the platform 24 into the larger portion of orifice 17 and grasping the opposed side. In the event that the disc 20 is frozen in place, a prying device may be used. The disc/specimen complex 61 is immediately placed into the first mounting member 55 for further processing.

The platform mounting device 54 is kept at a constant temperature of around −25° C. The corrugated disc 60 is placed into the second mounting member 56 and an amount of O.C.T. compound 65 is placed thereon. O.C.T. compound 65 is an embedding medium for frozen tissue specimens that is well-known in the art. O.C.T. is a abbreviation for "Optimum Cutting Time". O.C.T. compound is sold under the mark TISSUE TEK II by Miles Scientific, a Division of Miles Laboratories.

The O.C.T. compound 65 is also applied to the polished disc 20 by means of a bottle 66, as illustrated in FIG. 7, which also shows that O.C.T. compound 65 has been applied to the corrugated disc 60. The polished disc 20 is secured into the first mounting member by means of tightening the set scre 62 against the stem 25. The O.C.T. compound 65 is allowed to partially solidify, and the first mounting member is inverted and received onto the second mounting member alignment spindles 58, with an exposed surface of the tissue specimen 22 embedded in the O.C.T. compound 65, as seen in FIG. 8. The extremely cold mated platform mounting device 54 is kept in the position shown in FIG. 8 for a time sufficient to allow the O.C.T. compound 65 to solidify. The two mounting members 55 and 56 are subsequently separated, leaving the corrugated disc 60 frozen to the tissue specimen 22. The polished disc 20 is retained in the first mounting member 55 by means of the set screw 62. As seen in FIG. 9, the operator can remove the corrugated disc 60 by pulling it away from the polished disc 20. Since the polished disc 20 is smooth and coated with an anti-stick material, the O.C.T. compound 65 adheres to the corrugated disc 60 and is removed with it. The O.C.T. compound 65 will carry the embedded tissue specimen 22 with it, which presents a smooth, planar surface ready for processing in a microtome to produce uniform frozen sections for use in Mohs microscopically controlled surgery.

If the polished disc/specimen-O.C.T. compound-/corrugated disc complex fails to separate easily, the polished disc stem 25 may be placed into a heat source, which will enable it to be removed.

FIG. 10 represents the use of an alternative corrugated platform 64, which may be substituted in the noted method for the corrugated disc 60 and is designed to be used with a different type of cryostat.

The reference numeral 100 generally designates a modified apparatus for converting a tissue specimen 101 which has just been removed from a patient undergoing a Mohs surgical procedure or the like to a solidified structure having a generally planar exposed surface suitable for slicing and thereafter testing to determine the presence or absence of cancer or the like in the deepest layer of the tissue. The modified apparatus 101 is illustrated in FIGS. 12 through 23.

The apparatus 100 is similar in many respects to the apparatus 1 and, therefore, major differences will be discussed in greater detail, whereas similarities will be discussed in less detail. The apparatus 100 includes a support structure 105, a specimen support platform 106 having a generally planar specimen support surface 107 thereon, a vacuum generation mechanism 108, slot means comprising slot 109, freezing or refrigeration means comprising refrigeration mechanism 110 and transfer means comprising transfer platform 111.

The support platform 106 is mounted upon the support structure 105. The support platform 106 comprises a rectangularly shaped block 115 having an upwardly opening elongate channel 116 located therein. The block 115 has a generally planar upper surface 117. Positioned within the channel 116 is an elongate member 118 generally similar in shape to the channel 116 but slightly smaller in both length and width so as to define the slot 109 therebetween. Positioned on the upper side of the elongate member 118 is the support surface 107 which is substantially planar and generally coplanar with the block top 117.

The elongate member 118 includes a lower portion 121 constructed of clear plastic or the like and an upper, preferably metallic, plate 122 having a relatively high heat transfer coefficient and being secured to the lower portion 121 by suitable fasteners 123. The upper plate 122 has the support surface 107 on the upper side thereof and the surface 107 is preferably relatively smooth or polished. The lower portion 121 includes a serpentine channel 126 passing therethrough connected with an inlet port 127 and an outlet port 128. The slot 109 generally completely surrounds or encircles the periphery of the support surface 107.

The vacuum generation mechanism 108 includes a vacuum pump 131 joined by a conduit 132 through a port 133 with the slot 109 below the surface 107. In this manner, the vacuum pump 131, when actuated, draws air through the conduit 132 and port 133 from the slot 109. Preferably, the spacing between the block 115 and elongate member 118 is relatively close at the support surface 107 such that the slot 109 is relatively narrow around the entire periphery of the surface 107.

Mounted on the support structure 105 is a membrane dispensing mechanism 136 comprising a roll 137 rotatably mounted on supports 138 and having a web or membrane 139 wrapped thereabout. The membrane 139 is preferably a clear plastic-like pliable and flexible material drawable about an object by an applied vacuum, as described herein. A suitable membrane 139 may be constructed of polyethylene, polyvinyl or other similar flexible plastics and particular membranes of this type are sold under the trademarks Saran Wrap and cellphane. The width of the membrane 139 is preferably substantially wider than the longer side of the surface 107. The membrane dispensing mechanism 136 is positioned such that the membrane 139 may be easily rolled from the roll 137 into covering relationship to the surface 107.

Also mounted on the support structure 105 is a transfer means precooling and support member 145 held in place by a pair of uprights 146. The support member 145 is interiorly channeled and has a metallic upper plate 148. The support member channel 147 is connected to a conduit 155 which is, in turn, connected to the outlet port 128 associated with the channel 126.

The port 127 of the channel 126 is connected to a conduit 156 which is, in turn, connected to a gas distribution nozzle 157 associated with the refrigeration mechanism 110. In this manner, when the refrigeration mechanism is actuated by opening of the valving mechanism 157, refrigerating fluid at a temperature substantially less than ambient temperature passes through the conduit 156, through the channel 126, through the conduit 155, through the channel 147 and is either exhausted therefrom into the air or into a suitable disposal system. The refrigeration mechanism 110 may include previously cooled cryogenic liquids that have been cooled to approximately $-25°$ C. or the like, or a gas under relatively high pressure which cools substantially upon expansion after being released from the mechanism 110 into the conduit 156. A suitable gas of this type is carbon dioxide, although it is foreseen that other gasses such as nitrous oxide, freon and the like may be utilized for this system.

The transfer platform 111 comprises a disc 167 mounted upon a coaxially aligned shaft 168 and having a generally planar surface 169 opposite the shaft. The surface 169 is preferably corrugated or roughened as is shown in FIG. 22 to encourage sticking thereto by embedding medium as will be discussed hereinafter. The transfer platform 111 also preferably has associated therewith a positioning jig 172 which is illustrated in FIGS. 21 and 23. The illustrated jig 172 has the shape of a channel section having legs 173 and a crosspiece 174. Centered in the crosspiece 174 is an aperture 175 aligned with a coaxial sleeve 176. The sleeve 176 is sized to snugly receive the shaft 168 and ensure that, when the shaft 168 is slidably mounted in the sleeve 176 and the jig 172 is positioned so the legs 173 are supported by the surface 107, then the surface 169 will be substantially parallel to the surface 107.

Although a particular jig 172 has been shown and illustrated, it is foreseen that the jig could also be constructed with peg-like legs which would be received in suitable recesses in the block top 117 so as to further stabilize the jig 172 as it is being used for the purpose described below. That is, the jig could be constructed similar to the structure shown in FIG. 7 which includes circular legs and corresponding mating bores in the opposite disc.

Also seen in FIGS. 19 through 23 is a collar 178 comprising an elongate strip and embedding medium 179 transferred to a container 180. The collar 178 is formed of an elongate strip joined at opposite ends in a manner to be separable for an operator after use with the embedding medium 179. The collar 178 may be flexible, but must be of sufficient rigidity to stand upright on an edge thereof while being filled with mechanism 179, as described below.

The apparatus 100 is, in many ways, utilized in the same fashion as the apparatus 1 with some differences as discussed in detail below. Although not the only differences with the prior embodiment, four significant differences between the present embodiment and apparatus 1 are: the support surface 107 is fixed in position; cryogenic cooling medium is circulated under the surface 107 and cooling is transferred therethrough to the specimen 101; a wraparound collar 178 is used to hold the embedding medium 179 until it solidifies; and drawing of a vacuum through the slot 109 is sufficient to retract the membrane 139 totally around the specimen 101 such that the specimen is urged against the surface 107 without supplemental sealing means for the membrane 139.

In particular, the tissue specimen 101 is surgically removed from a patient and transferred to the apparatus 100. The specimen 101 typically has a parabolic or at least a somewhat curved undersurface 185 which is very difficult to make planar because of its curvature and natural resiliency. The specimen 101 is positioned on the support surface 107 such that the tissue undersurface 185 is in direct contact with or directly positioned over the support surface 107, as seen in FIG. 15. The operator thereafter unrolls the membrane 139 from the roll 137 such that the membrane 139 covers the tissue 101, the entire support surface 107 and the slot 109. Thereafter, the vacuum pump 131 is activated so as to draw air through the conduit 132 and, consequently, through the slot 109 which, in turn, draws the membrane 139 snugly against the slot 109. Simultaneously, the air is drawn from between the membrane 139 and the specimen 101 as well as the surface 107. Preferably, the vacuum is applied slowly by means of an operator controlled reostat or valve at the pump 131 so as to allow the operator to readjust the specimen 101 to an optimum configuration. The membrane 139 is thus snugly drawn downwardly or retracted against the surface 107 and this, in turn, urges or biases the tissue specimen 101 into contact with the surface 107 entirely along the undersurface 185 thereof. As can be seen in FIG. 17, the operator may manually manipulate the specimen 101 through the membrane 139 while air is being withdrawn by the vacuum pump 131 so as to facilitate production of a vacuum within the region beneath the membrane 139 and surrounding the specimen 101.

Subsequent to the undersurface 185 of the specimen 101 being substantially flattened against the surface 107, the refrigeration mechanism 110 is operated b opening the valve 157 to allow compressed gas to escape to the lower pressure in conduit 156 as well as the subsequent path of the gas. This substantially drops the temperature of the structure surrounding the channels 126 and 147 and specifically substantially cools the plates 121 and 148. As the plate 121 cools, heat is transferred from the tissue specimen 101 thereby causing it to cool. Preferably, the specimen 101 is substantially frozen to temperatures of −25° C. or the like and, thereby, cryosolidified. The transfer plate 111 and jig 172 are positioned on the plate 148 prior to use and are consequently precooled as the plate 148 is cooled.

After the tissue specimen 101 has been allowed to thoroughly become solidified, the vacuum pump 131 is deactivated and the membrane 139 is peeled from the top of the surface 107 and from the top 186 of the specimen, as can be seen in FIG. 18. Thereafter, the collar 178 is positioned around the specimen 101 such that the collar 178 sits upon the surface 107 and extends above the specimen 101. This can be seen in FIG. 19 where a collar has been positioned upon the specimen 101 on the right hand side and is about to be positioned around the next specimen 101.

After the collar 178 is positioned around the specimen 101, embedding medium 179 is deposited within the collar 178 so as to completely cover the specimen 101 and, thereafter, allowed to solidify due to the cooling of the refrigeration mechanism 110.

The transfer platform 111 having a disc 167 with a diameter substantially similar to the diameter of the collar 178 when in place, is positioned over the embedding medium 179 preferably before being totally solidified and specimen top 186, such as is seen in FIG. 21. In particular, the surface 169 is positioned in facing relationship to the surface 109 as well as to the specimen top 186 and biased downwardly into the medium 179 so as to evenly engage the upper surface of the medium 179 and eventually become stuck thereto. Because of the corrugations on the surface 169 and because the surface 107 includes release means such as being constructed of a non-stick material, sprayed with a non-sticking agent, being highly polished or being coated with a fixed layer of an anti-sticking composition; the embedding compound 179 with the specimen 101 therein as well as the collar 178 therearound preferably stick to the surface 169 and are released by the release means from the surface 107.

It is noted that the transfer platform 111 is carefully placed in a transfer orientation by the jig 172 such that the surface 169 is parallel to the surface 107 and more particularly so the surface 169 is parallel to the tissue undersurface 185. Subsequent to a release of the embedding compound 179 and tissue specimen 101 from the surface 107, the undersurface 185 is exposed, generally planar and aligned so as to be substantially parallel to the surface 169 as well as perpendicular to the shaft 168 such that the specimen 101 is now in condition for transfer to a cryostat or other suitable slicing mechanism for producing slices to review to determine if carcinogenic material is present. Prior to transfer to the cryostat (not shown), the collar 178 is peeled away, such as is shown in FIG. 23, leaving the specimen 101 mounted on the transfer-platform 111 with the undersurface 185 exposed and held securely in the solidified embedding medium 179.

It is noted that, in the present embodiment, the membrane 139 functions as its own sealing means in that the membrane 139 is sealed against the outer periphery of the surface 107 by the vacuum drawn through the slot 109 thereby drawing the membrane 139 snugly against the slo 109.

It is noted that, although a particular transfer platform 111 has been described having a circular disc 167 and being suited for use with a particular cryostat or other sectioning device, other shaped transfer platforms constructed to be compatable with other cryostats or the like could be used interchangeably with the illustrated transfer platform 111.

It is to be understood that while certain forms of the present invention have been illustrated and described herein, it is not to be limited to the specific forms or arrangement of parts described and shown.

What is claimed and desired to be secured by Letters Patent is as follows:

1. An apparatus for preparing a tissue specimen for sectioning in a microtome or the like; said apparatus comprising:
   (a) a vacuum receptacle assembly having an interior chamber;
   (b) a vacuum source operatively connected to said vacuum receptacle assembly for drawing air from said vacuum receptacle assembly chamber;
   (c) a platform having a surface for receiving the specimen;
   (d) said vacuum receptacle assembly having means for receiving and retaining said platform;
   (e) a flexible membrane for covering said platform when said platform and specimen are retained by said vacuum receptacle assembly;
   (f) sealing means for creating a seal between said membrane and said vacuum receptacle assembly, whereby upon activation of said vacuum source air is drawn from said vacuum receptacle assembly chamber; and
   (g) means for freezing the tissue specimen to said platform.

2. The apparatus as set forth in claim 1 wherein:
   (a) said vacuum receptacle assembly includes a receptacle structure having an interior chamber in airflow communication with said vacuum source;
   (b) said vacuum receptacle assembly includes a baseplate attached to an upper portion of said receptacle structure, said baseplate having an orifice for providing airflow communication with said interior chamber, said baseplate further including a recessed step portion generally centered about said baseplate orifice and sized to receive said platform; and
   (c) said vacuum receptacle assembly including a cover plate connected to said baseplate and movable into a covering position over said baseplate, said cover plate having an orifice therethrough for providing access to said platform when said platform is received in said vacuum receptacle assembly.

3. The apparatus as set forth in claim 2 wherein:
   (a) said platform includes a generally circular polished surface and a stem depending therefrom; and
   (b) said baseplate orifice includes a portion through which said stem extends when said platform is received by said vacuum receptacle assembly, said baseplate orifice further including an elliptical portion for providing means for tipping said platform for removal thereof from said vacuum receptacle assembly.

4. The apparatus as set forth in claim 2 wherein said sealing means comprises:
   (a) said baseplate;
   (b) said cover plate; and
   (c) an O-ring attached to one of said cover plate and baseplate in a surrounding position about said baseplate step portion for sealing said flexible membrane relative to said vacuum receptacle assembly.

5. The apparatus as set forth in claim 4 wherein:
   (a) said O-ring is connected to said cover plate; and
   (b) said cover plate is connected to said baseplate by hinge means; said hinge means including spring-loaded bolts swingably attached to said cover plate and extending through said baseplate, said spring-loaded bolts having means for biasing said cover plate toward said baseplate.

6. The apparatus as set forth in claim 5 including a spring-loaded locking shaft connected to said cover plate and adapted to extend through said baseplate for releasably fastening said cover plate to said baseplate in said covering position.

7. The apparatus as set forth in claim 1 wherein said membrane is made from a flexible, transparent plastic film material for permitting manipulation of said specimen by an operator while maintaining said specimen in a generally planar relationship when said vacuum source is activated.

8. The apparatus as set forth in claim 1 wherein said platform includes:
   (a) a generally circular polished surface for receiving the tissue specimen, said polished platform surface being coated with a non-stick material and having score lines thereon extending radially from a center of said surface; and
   (b) a stem depending from a center of said platform opposite said surface.

9. The apparatus as set forth in claim 1 including:
   (a) a platform mounting device for receiving said platform and specimen upon freezing thereof to said platform, said platform mounting device including:
      (1) a first mounting member for receiving said platform and tissue specimen;
      (2) a second mounting member for receiving a transfer disc for receiving said tissue specimen from said platform;
      (3) said first and second mounting members being mateable to one another for aligning said platform and said transfer disc with one another;
   (b) an embedding medium for placement between said transfer disc and said platform with said specimen frozen therein, said embedding medium facilitating the transfer of said tissue specimen from said platform to said transfer disc upon mating of said first and second mounting members.

10. An apparatus for preparing a tissue specimen for sectioning in a microtome or the like; said apparatus comprising:
   (a) a platform having a generally planar surface thereon;
   (b) vacuum source means;
   (c) said surface having slot means around a periphery thereof; said slot means in selective communication with said vacuum source means such that said vacuum source means draws air from slot means;
   (d) flexible membrane means for providing a membrane in covering relation to said planar surface, said slot means and said specimen, when said specimen is positioned on said surface;

(e) means for freezing the tissue specimen to said platform;

(f) whereby when said membrane is placed over said specimen, surface and slot means and upon activation of said vacuum source means, air is drawn from said slot means and from between said membrane and said surface thereby drawing said membrane snugly against the specimen, surface and slot means such that an underside of the specimen is generally flattened against said surface.

11. The apparatus according to claim 10 wherein:

(a) said slot means comprises a relatively narrowly upward opening slit completely encircling said planar surface.

12. The apparatus according to claim 10 including:

(a) channel means within said platform; and (b) refrigeration means communicating with said channel means and selectively providing a source of coolant therethrough.

13. The apparatus according to claim 11 wherein:

(a) said channel means comprises a serpentine conduit passing beneath and in relatively close association to said planar surface.

14. The apparatus according to claim 11 including:

(a) a collar adapted to surround the tissue specimen when on said surface and for receiving embedding medium therein.

15. The apparatus according to claim 14 wherein:

(a) said platform is a first platform and said surface is a first surface; and including (b) a transfer second platform having a second planar surface thereon; said second surface adapted to be positionable upon said embedding medium and the tissue specimen, while the specimen is on said first surface such that the specimen is between said first and second surfaces; said first surface including release means thereon to allow release of the specimen to said second surface.

16. The apparatus according to claim 15 including:

(a) a support jig cooperating with said second platform to ensure said second surface is positioned generally parallel to said first surface when in a transfer orientation thereof.

* * * * *